US00PP26307P3

(12) United States Plant Patent
Barrault

(10) Patent No.: US PP26,307 P3
(45) Date of Patent: Jan. 12, 2016

(54) ***GAURA* PLANT NAMED 'BARGAU'**

(50) Latin Name: *Gaura lindheimeri*
Varietal Denomination: BARGAU

(71) Applicant: Michel Barrault, La Possonniere (FR)

(72) Inventor: Michel Barrault, La Possonniere (FR)

( * ) Notice: Subject to any disclaimer, the term of this patent is extended or adjusted under 35 U.S.C. 154(b) by 181 days.

(21) Appl. No.: 13/987,631

(22) Filed: Aug. 16, 2013

(65) Prior Publication Data

US 2015/0052652 P1 Feb. 19, 2015

(51) Int. Cl.
*A01H 5/02* (2006.01)

(52) U.S. Cl.
USPC ..... Plt./432
CPC ..... *A01H 5/02* (2013.01)

(58) Field of Classification Search
USPC ..... Plt./432, 226
See application file for complete search history.

(56) References Cited

PUBLICATIONS

Les Jardins de la Boirie, *Gaura lindheimeri* Pink Panache, retrieved on Apr. 2, 2015, retrieved from the Internet at <www.lesjardinsdelaboirie.com/2012/09/gaura-lindheimeri-pink-panache.html> Sep. 14, 2012, 4 pp.*

New Plants and Flowers, Variegated new prolific *Gaura,* Jan. 19, 2013, retrieved on Apr. 2, 2015, retrieved from the Internet at <http://www.newplantsandflowers.com/variegated-new-prolific-gaura/> 2 pp.*

Les Jardins de la Boirie English translation, 4 pp.*

* cited by examiner

*Primary Examiner* — June Hwu
(74) *Attorney, Agent, or Firm* — Cassandra Bright

(57) ABSTRACT

A new and distinct *Gaura lindheimeri* cultivar named 'BARGAU' is disclosed, characterized by compact plants, immature stems and foliage flushed with red-purple coloration. Foliage becomes green and yellow variegated with age and plants branch easily. The new variety is a *Gaura*, and is normally used as an ornamental garden or container plant.

3 Drawing Sheets

Latin name of the genus and species: *Gaura lindheimeri.*
Variety denomination: 'BARGAU'.

BACKGROUND OF THE INVENTION

The new cultivar is a product of chance discovery. The variety was discovered as a naturally occuring whole plant mutation at a commercial nursery by the inventor, Michel Barrault, a citizen of France. The new variety was discovered among a commercial population of the unpatented variety *Gaura lindheimeri* 'Siskyou Pink', during 2010.

Asexual reproduction of the new cultivar 'BARGAU' was first performed by vegetative stem cuttings in Possonniere, France at a commercial nursery. 'BARGAU' has since produced more than 5 generations by vegetative cuttings and has shown that the unique features of this cultivar are stable and reproduced true to type.

SUMMARY OF THE INVENTION

The cultivar 'BARGAU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BARGAU'. These characteristics in combination distinguish 'BARGAU' as a new and distinct *Gaura lindheimeri* cultivar:

1. Compact plants.
2. Variegated foliage.
3. Young stems and foliage flushed with red coloration.

4. Good branching habit.
5. Pink flowers.

PARENT COMPARISON

Plants of the new cultivar 'BARGAU' are similar to plants of the parent variety, *Gaura lindheimeri* 'Siskyou Pink' in most horticultural characteristics. However, plants of the new cultivar 'BARGAU' produce variegated foliage not found in the parent variety. In addition, 'BARGAU' is more compact and forms a denser, and bushier plant than 'Siskyou Pink'.

COMMERCIAL COMPARISON

Plants of the new cultivar 'BARGAU' are similar to plants of the commercial variety, *Gaura lindheimeri* 'Passionate Rainbow' U.S. Plant Pat. No. 17,002. Plants of the new cultivar produce young foliage with a stronger red coloration than that of 'Passionate Rainbow'. Additionally, foliage color of 'BARGAU' changes to a bright yellow and green as plants mature, whereas foliage of 'Passionate Rainbow' is cream and green. Overall plant formation of 'BARGAU' is denser and more compact than 'Passionate Rainbow'.

Plants of the new cultivar 'BARGAU' are similar to plants of the commercial variety, *Gaura lindheimeri* 'Corrie's Gold', unpatented. Plants of the new cultivar are more upright with better branching than plants of 'Corrie's Gold'. Additionally, plants of 'BARGAU' produce red coloration on immature stems and foliage, whereas foliage of 'Corrie's Gold' is cream and white. Flower color of the new variety is pink, whereas 'Corrie's Gold' produces a white flower.

BRIEF DESCRIPTION OF THE PHOTOGRAPHS

The accompanying photograph in FIG. 1 illustrates in full color a typical plant of 'BARGAU' grown in a outdoors. The plant is shown in an approximately 2 gallon pot.

DETAILED BOTANICAL DESCRIPTION

Figure 1:
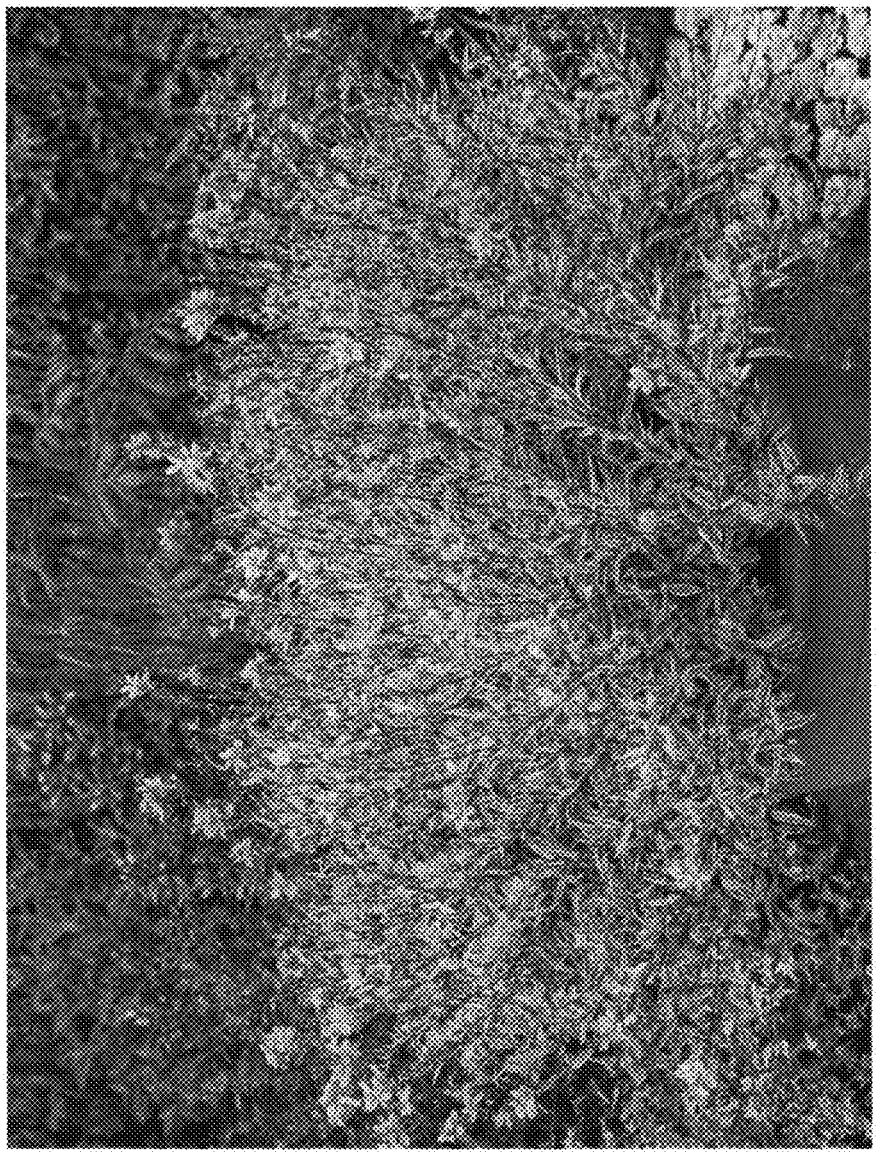
Figure 2:
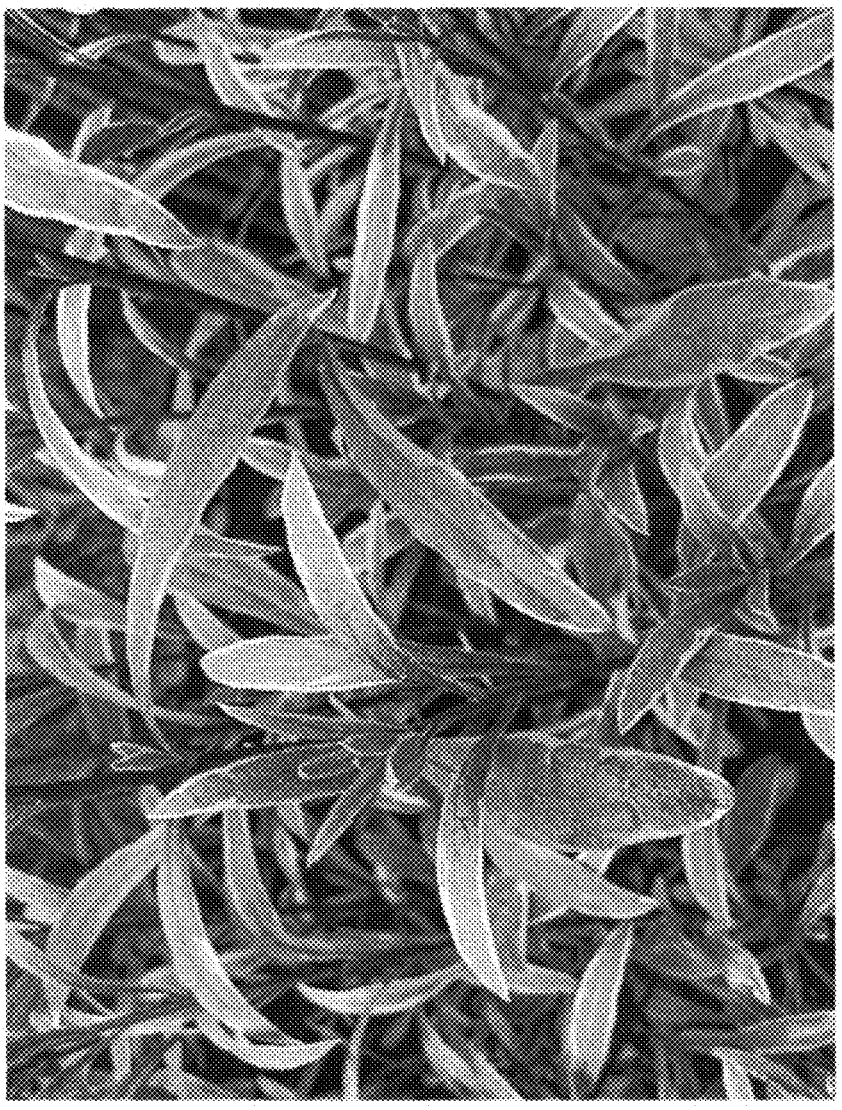
FIG. 2 illustrates a close-up detail of immature foliage.
Figure 3:
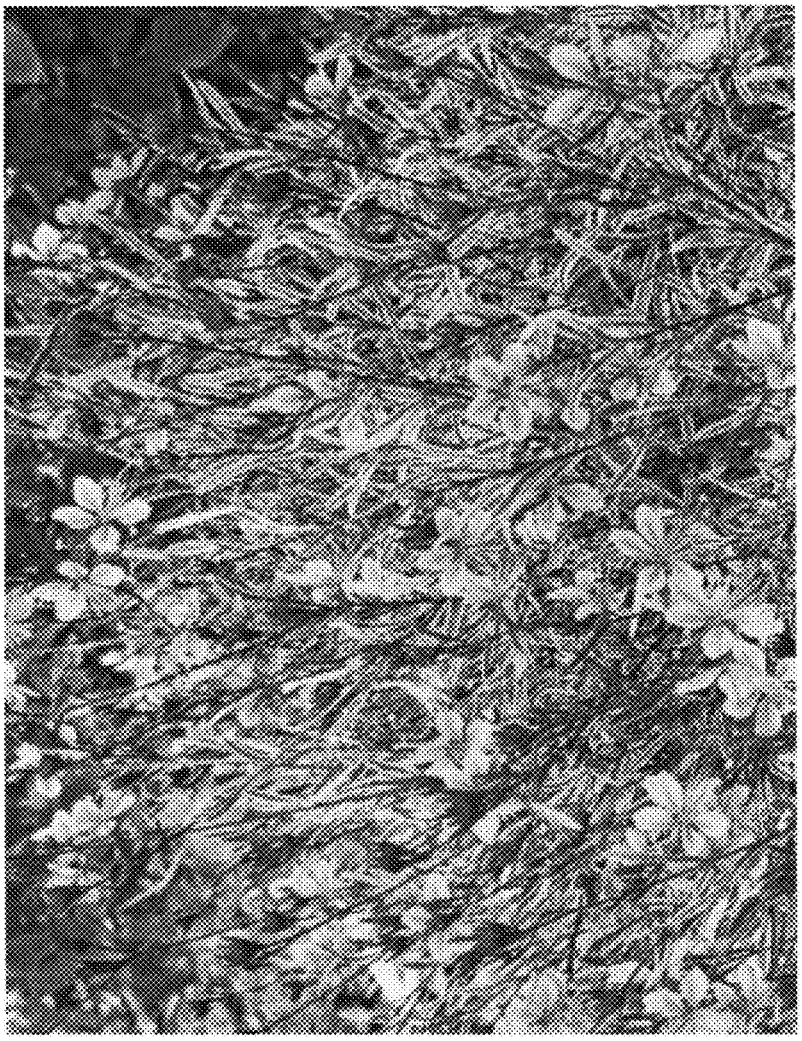
FIG. 3 illustrates a close up of mature flowers and foliage.

In the following description, color references are made to The Royal Horticultural Society Colour Chart 2007 except where general terms of ordinary dictionary significance are used. The following observations and measurements describe 'BARGAU' plants outdoors in a commercial nursery in Possonniere, France. Temperatures ranged from approximately 5° C. to 35° C. during the day and −2° C. to 22° C. at night. No artificial light, photoperiodic treatments or chemical treatments were given to the plants. Measurements and numerical values represent averages of typical plant types.

Botanical classification: *Gaura lindheimeri* 'BARGAU'.

PROPAGATION

Time to initiate roots: 15 to 20 days at approximately 20° C.

Root description: Fibrous, colored near RHS Greyed-Orange 165D.

PLANT

Growth habit: Compact, upright perennial.

Pot size of plant described: 2 gallon.

Height: 50 to 60 cm.

Plant spread: Approximately 70 to 80 cm.

Growth rate: Rapid.

Branching characteristics: Basal branching, or nearly at soil level. Lateral branches produced approximately 5.0 cm above pinch to main stem. Upper lateral branches not produced.

Length of primary branches: Approximately 45 cm.

Diameter of branches: Approximately 0.35 cm.

Quantity of primary branches: Average 50.

Characteristics of primary lateral branches:

- *Form*.—Irregular round, some flat sides.
- *Color*.—Immature branches Near RHS Red-Purple 59B. Mature branches near Greyed-Purple 187B.
- *Texture*.—Scant pubescence.
- *Strength*.—Strong, somewhat flexible.

Internode length.—1.0 to 3.0 cm.

FOLIAGE

Leaf:

- *Arrangement*.—Alternate, simple.
- *Quantity*.—Approximately 12 to 20 fully developed per branch. General quantity few for a typical *Gaura*.
- *Average length*.—5.0 cm.
- *Average width*.—1.4 cm.
- *Shape of blade*.—Elliptic.
- *Apex*.—Acute.
- *Base*.—Attenuate.
- *Margin*.—Entire.
- *Texture of top surface*.—Scant pubescence visible under magnification.
- *Texture of bottom surface*.—Glabrous.
- *Aspect*.—Flat with undulation at apex.
- *Color*.—Young foliage upper side: Near RHS Greyed-Green 191A with irregular marginal variegation near Green-White 157D. Heavily flushed Red-Purple 59B and 59C. Flushing is heaviest from base. Young foliage under side: Near RHS Greyed-Green 191 A with irregular marginal variegation near Green-White 157D. Heavily flushed Red-Purple 59B and 59C. Flushing is heaviest from base. Mature foliage upper side: Near RHS Green 137D, margin Yellow 9D. Mature foliage under side: Near RHS Green 137D, margin Yellow 9D.
- *Venation*.—Type: Pinnate. Mature Foliage: Venation color upper side: Near RHS Yellow 9D. Venation color under side: Near RHS Yellow 9D. Young Foliage: Venation color upper side: Lower 75% near RHS Red-Purple 64A. Near apex Red-Purple 65B, and Yellow 4D. Venation color under side: Near RHS Red-Purple 64A. Near apex occasionally near Yellow 4D.
- *Petiole*.—Sessile.

FLOWER

Natural flowering season: Spring through Summer.

Inflorescence and flower type and habit: Single zygomorphic flowers produced on terminal and axillary racemes.

Persistent or self-cleaning: Self Cleaning.

Bud:

- *Shape*.—Cylindric.
- *Length*.—2.0 cm.
- *Diameter*.—0.5 cm
- *Color*.—Near RHS Red-Purple 59C.

Raceme:

- *Diameter*.—Average 5 cm.
- *Length*.—Average 15 cm.
- *Flowers per raceme*.—5 to 9.

Flower size:

- *Diameter*.—Average 2.5 cm.
- *Length*.—Average 2.5 cm.

Corolla/petals:

- *Quantity of petals*.—4.
- *Arrangement*.—Symmetrical whorl.
- *Petal length*.—2.0 cm.
- *Petal width*.—1.0 cm.
- *Corolla tube length*.—1.5 cm.
- *Corolla tube diameter*.—0.2 cm.
- *Texture*.—Glabrous.
- *Petal apex*.—Acute.
- *Petal base*.—Attenuate.
- *Petal shape*.—Spatulate.
- *Margin*.—Entire.
- *Aspect*.—Upwardly cupped.
- *Petal color*.—When opening: Upper surface: Near RHS Red-Purple 59C. Lower surface: Near RHS Red-Purple 59C. Fully opened: Upper surface: Near RHS Red-Purple 61C, thick margin Red-Purple 65D. Center vein Red-Purple 59C. Lower surface: Near RHS Red-Purple 61C, thick margin Red-Purple 65D. Center vein Red-Purple 59C. Fading: Upper surface: Near RHS Red-Purple 62D, thick margin Red-Purple 65D. Center vein Red-Purple 61D. Lower surface: Near RHS Red-Purple 62D, thick margin Red-Purple 65D. Center vein Red-Purple 62C.
- *Outer corolla tube color*.—Near RHS Red-Purple 58C.
- *Inner corolla tube color*.—Near RHS Green 137D with heavy flush Red-Purple 58C.

Calyx/sepals:
*Quantity per flower.*—4.
*Shape.*—Linear.
*Length.*—1.7 cm.
*Width.*—0.3 cm.
*Apex.*—Acute.
*Base.*—Truncate.
*Margin.*—Entire.
*Texture.*—Glabrous.
*Aspect.*—Undulating and strongly reflexed back.
*Color.*—Upper Surface: Near RHS Red-Purple 58C. Lower Surface: Near RHS Red-Purple 59A.

Peduncle:
*Length.*—Average 10.5 cm.
*Diameter.*—Approximately 0.2 cm.
*Color.*—Near RHS Green 137A flushed with Greyed-Purple 187B.
*Orientation.*—Straight, approximately 15 degree angle from stem.
*Texture.*—Glabrous.
*Strength.*—Strong.

Pedicel: Not present, directly attached by corolla tube to peduncle.

Fragrance: Not observed.

REPRODUCTIVE ORGANS

Stamens:
*Number.*—8.
*Filament length.*—Approximately 1.4 cm.
*Filament color.*—Near Red-Purple 59A.

Anthers:
*Shape.*—Linear.
*Length.*—Approximately 0.3 cm.
*Color.*—Near RHS Greyed-Purple 187A.
*Pollen.*—Color: Near RHS Orange-White 159A. Quantity: Scant.

Pistil:
*Number.*—1.
*Length.*—2.7 cm.
*Style.*—Length: 2.5 cm. Color: Near RHS Red-Purple 69A with upper portion Red-Purple 61C.
*Stigma.*—Shape: Bi lobed. Color: Near RHS Green-White 157A.
*Ovary.*—Ovary Color: Near RHS Greyed-Purple 187B. Ovary Length: Approximately 1 cm. Ovary diameter: Approximately 0.1 cm Ovary shape: Linear.

OTHER CHARACTERISTICS

Seeds and fruits: Not observed to date.

Disease/pest resistance: Neither resistance nor susceptibility to diseases or pests has been observed in this variety.

Temperature tolerance: The new variety tolerates temperatures from approximately −10° to 40° C.

What is claimed is:

1. A new and distinct cultivar of *Gaura* plant named 'BARGAU' as herein illustrated and described.

* * * * *